US012758346B2

(12) United States Patent
Huisinga et al.

(10) Patent No.: US 12,758,346 B2
(45) Date of Patent: Oct. 13, 2026

(54) BODY-WEARABLE MEDICAL DEVICE WITH A SEALING ELEMENT

(71) Applicant: Roche Diabetes Care, Inc., Indianapolis, IN (US)

(72) Inventors: Matthias Huisinga, Frankenthal (DE); Liang Yi Li, New Taipei (TW); Chun-Wei Liu, Hsinchu County (TW)

( * ) Notice: Subject to any disclaimer, the term of this patent is extended or adjusted under 35 U.S.C. 154(b) by 0 days.

(21) Appl. No.: 18/798,437

(22) Filed: Aug. 8, 2024

(65) Prior Publication Data

US 2024/0398499 A1 Dec. 5, 2024

Related U.S. Application Data

(63) Continuation of application No. PCT/EP2023/053036, filed on Feb. 8, 2023.

(30) Foreign Application Priority Data

Feb. 10, 2022 (EP) .................................... 22156022

(51) Int. Cl.
*A61B 50/30* (2016.01)
*A61B 50/00* (2016.01)

(52) U.S. Cl.
CPC ........ *A61B 50/30* (2016.02); *A61B 2050/002* (2016.02)

(58) Field of Classification Search
CPC ............. A61B 50/30; A61B 2050/002; A61M 2005/14264; A61M 2005/14268; A61M 2205/0216; A61M 5/14244
See application file for complete search history.

(56) References Cited

U.S. PATENT DOCUMENTS 7,510,544 B2 3/2009 Vilks et al.
10,154,617 B2 12/2018 Hauer
(Continued)

FOREIGN PATENT DOCUMENTS

DE 10 2005 053 765 A1 5/2007
EP 1 296 598 B1 11/2007
TW 200950833 A 12/2009

OTHER PUBLICATIONS

International Search Report and Written Opinion of the International Searching Authority, PCT/EP2023/053036, Feb. 28, 2023, 8 pages.

*Primary Examiner* — Chinyere Mpamugo
(74) *Attorney, Agent, or Firm* — Bose McKinney & Evans LLP

(57) ABSTRACT

A body-wearable medical device has first and second housing portions. The first housing portion has a female portion and the second housing portion has a male portion. The male portion is at least partially inserted into the female portion, thereby defining a circumferential clearance gap. A circumferential sealing element is arranged in the circumferential clearance gap between the female portion and the male portion. In order to provide a body-wearable medical device with improved sealing that is less prone to failure by stress and forces exerted on the body-wearable medical device, the female portion and the male portion are fixed to each other by a circumferential fixation glue arranged in the circumferential clearance gap between the female portion and the male portion next to the circumferential sealing element.

10 Claims, 2 Drawing Sheets

(56) References Cited

U.S. PATENT DOCUMENTS

| | | | | |
|---|---|---|---|---|
| 11,298,459 | B2 * | 4/2022 | Du | G16H 20/17 |
| 2003/0163090 | A1 | 8/2003 | Blomquist et al. | |
| 2009/0001553 | A1 | 1/2009 | Pahl et al. | |
| 2009/0293887 | A1 | 12/2009 | Wilkes et al. | |
| 2010/0106091 | A1 | 4/2010 | Wright et al. | |
| 2017/0359924 | A1 | 12/2017 | Hauer | |
| 2019/0083809 | A1 * | 3/2019 | Zhang | A61N 5/0616 |
| 2022/0160954 | A1 * | 5/2022 | Carter | A61M 5/168 |

* cited by examiner

BODY-WEARABLE MEDICAL DEVICE WITH A SEALING ELEMENT

RELATED APPLICATIONS

This application is a continuation of International Application Serial No. PCT/EP2023/053036, filed Feb. 8, 2023, which claims priority to European Patent Application Serial No. 22 156 022.0, filed Feb. 10, 2022, the entire disclosures of both of which are hereby incorporated herein by reference

BACKGROUND

This disclosure relates to a body-wearable medical device comprising a first housing portion and a second housing portion, the first housing portion having a female portion and the second housing portion having a male portion, the male portion being at least partially inserted into the female portion, thereby defining a circumferential clearance gap. A circumferential sealing element is arranged in the circumferential clearance gap between the female and male portions.

A body-wearable medical device is a small, relatively lightweight device that during its use is carried by a patient. Thus, the body-wearable medical device is exposed to the same environmental conditions and stress as the patient. Sometimes the body-wearable medical device is concealed by clothing, sometimes not. In order to prevent a malfunction caused by an ingress of dust, water, and/or humidity, the circumferential sealing is provided within the circumferential gap between the female portion and the male portion.

However, as the body-wearable medical device is carried by a user, the body-wearable medical device may not only be exposed to dust, water and humidity, but also may be exposed to forces and stress caused by the patient's movements and activities. For example, during sport or movements of the user, forces and stress are exerted on the body-wearable medical device that may cause a temporary deformation of the first housing portion and/or the second housing portion. Due to the temporary deformation of the first housing portion and/or the second housing portion, the width of the circumferential clearance gap between the female portion and the male portion may alter. A change of the width of the clearance gap may negatively affecting the sealing between the female portion and the male portion as provided by the sealing element.

SUMMARY

This disclosure teaches a body-wearable medical device comprising an improved sealing that is less prone to failure by stress and forces exerted on the body-wearable medical device.

These improvements are provided by a body-wearable medical device as outlined above, wherein the female portion and the male portion are fixed to each other by a circumferential fixation glue that is arranged in the circumferential clearance gap between the female portion and the male portion next to the circumferential sealing element.

The circumferential fixation glue helps maintain the position of the first housing portion relative to the second housing portion. The circumferential fixation glue at least partially fills the clearance gap between the female portion and the male portion. Furthermore, the circumferential fixation glue helps prevent part of the female portion and part of the male portion from being displaced from each other by stress or forces exerted on the body-wearable medical device. Thereby, the clearance gap is less likely deformed and the sealing element maintains its sealing function.

According to an embodiment, the sealing element is a sealing glue having a smaller elastic modulus than the fixation glue. The purpose of the fixation glue is to keep the female portion and the male portion within their relative positions, while the sealing glue prevents an ingress of at least one of water, dust, splash water and humidity. When providing a sealing element formed by a sealing glue, the sealing glue itself helps to keep the female portion and the male portion within their relative positions. Furthermore, the flexibility of the sealing glue helps to balance deformations of the clearance gap caused by stress and/or forces acting on the body-wearable medical device.

In an embodiment, the sealing glue is a polyurethane adhesive. In an embodiment, the polyurethane adhesive has a hardness of more than or equal to Shore A40 and lower than or equal to Shore A50. For example, the polyurethane adhesive has a hardness of Shore A42. According to an embodiment, the polyurethane adhesive has a viscosity of more than or equal to 30.000 millipascal-second, preferable more than or equal to 40.000 mPas, but lower than or equal to 90.000 mPas, preferably lower than or equal to 80.000 mPas.

In an embodiment, the fixation glue is a low odor acrylic adhesive. In an embodiment, at room temperature the full cure time is 8 to 24 hours, and the fixation glue has a shear strength of more than or equal to 20.000 MPa and lower than or equal to 30.000 MPa. For example, the acrylic adhesive can have a shear strength of 28.959 MPa.

In an embodiment, the sealing element comprises an O-ring arranged in the circumferential gap between the female and male portions that circumscribes the male portion. The O-ring is an elastic plastic ring circumscribing the male portion within the circumferential gap between the female portion and the male portion. The O-ring can form the sealing element as a standalone element, but can also form the sealing element together with the sealing glue. When being used together with the sealing glue, the O-ring is a reinforcement of the sealing element while the sealing glue helps to keep the sealing element in close sealing contact with the male portion and the female portion. The O-ring may additionally or alternatively form a barrier that is arranged next to the fixation glue and that helps to prevent the sealing glue from further ingressing into the housing.

In an embodiment, the fixation glue discontinuously circumscribes the male portion in the circumferential clearance gap between the female portion and the male portion. The fixation glue can continuously or discontinuously circumscribe the male portion at least partially filling the clearance gap between the male portion and the female portion. In the context of this disclosure, a discontinuously circumscribing fixation glue comprises multiple distinct fixation glue elements that are separated from each other along the circumference of the male portion within the clearance gap. Each of the distinct fixation glue elements is in contact with the male portion and the female portion thereby fixing the male portion and the female portion together. According to an embodiment, the sum of length of each of the distinct fixation glue elements is larger than 40% of the circumferential length of the male portion along the line of the distinct fixation glue elements. In an embodiment, the sum of length of each of the distinct fixation glue elements is larger than 50% of the circumferential length of the male portion along the line of the distinct fixation glue elements. The sum of length of each of the distinct fixation glue elements can be smaller than 80% or 70% of the circumferential length of the male portion along the line of the distinct fixation glue elements.

In an embodiment, the discontinuously circumscribing fixation glue is evenly distributed along the circumference of the male portion. Accordingly, the distinct fixation glue elements are evenly distributed along the circumferential length of the male portion within the clearance gap.

In an embodiment, the circumferential clearance gap is formed by a circumferential recess of the male portion and/or a circumferential recess of the female portion. Accordingly, the clearance gap can be formed by a recess in the male portion that extends along the circumference of the male portion. Alternatively, the clearance gap can be formed by a recess in the female portion that extends along the inner circumference of the female portion. Further alternatively, the clearance gap can be formed by both a recess in the female portion extending along the inner circumference of the female portion facing the male portion and a recess in the male portion extending along the outer circumference of the male portion facing the female portion.

According to an embodiment, the male portion comprises a free-end portion facing away from the first housing portion, wherein the sealing element is located closer to the free-end portion than the fixation glue. In an order from the free-end towards the insertion direction of the male portion, the sealing element is arranged closer to the free-end portion than the fixation glue. The sealing element forms an outer boundary while the fixation glue is arranged inward relative to the sealing element. As the male portion is at least partially inserted into the female portion, the free-end portion of the male portion can project out of the female portion or can be flush with the female portion. As mentioned earlier, the sealing element can comprise a sealing glue or can be formed by a sealing glue.

In an embodiment, the first housing portion and the second housing portion form a watertight compartment. By forming a watertight compartment the sealing element forms a watertight sealing that prevents an ingress of water through the clearance gap between the male portion and the female portion.

In an embodiment, in a cross-sectional view, the circumferential clearance gap forms a circular, a rectangular, a quadratic or elliptic shape circumscribing the male portion. The respective circular, rectangular, quadratic or elliptic shape circumscribing the male portion is formed by an inner wall portion of the female portion that faces the male portion. When viewed in a cross-sectional view, the inner wall portion of the female portion forms an outer boundary of the circumferential clearance gap.

In an embodiment, the rectangular or elliptic shape that, in a cross-sectional view of the body-wearable medical device, is formed by the circumferential clearance gap comprises a first extension in one direction and a second extension in a second direction. The first extension is at least 1.5 times larger than the second extension in the second direction. In an embodiment, the first extension is at least 2 times larger than the second extension in the second direction. In an embodiment, the first extension is at least 3 times larger than the second extension in the second direction. The first direction and second direction are perpendicular to each other.

According to an embodiment, the body-wearable medical device is a drug delivery device, in particular an insulin delivery device, such as, for example, an insulin pen or an insulin infusion pump. The body-wearable medical device can be a continuous glucose monitoring device or a body-wearable medical device that is configured for analyzing body fluids. The body-wearable medical device can comprise a plaster and/or an adhesive layer that is configured for temporarily adhering the body-wearable medical device to a patient's body. The body-wearable medical device can comprise a transcutaneous element such as, for example, a cannula, a probe or a sensor. The probe configured for retrieving body fluids, while the sensor is configured for analyzing body fluids.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
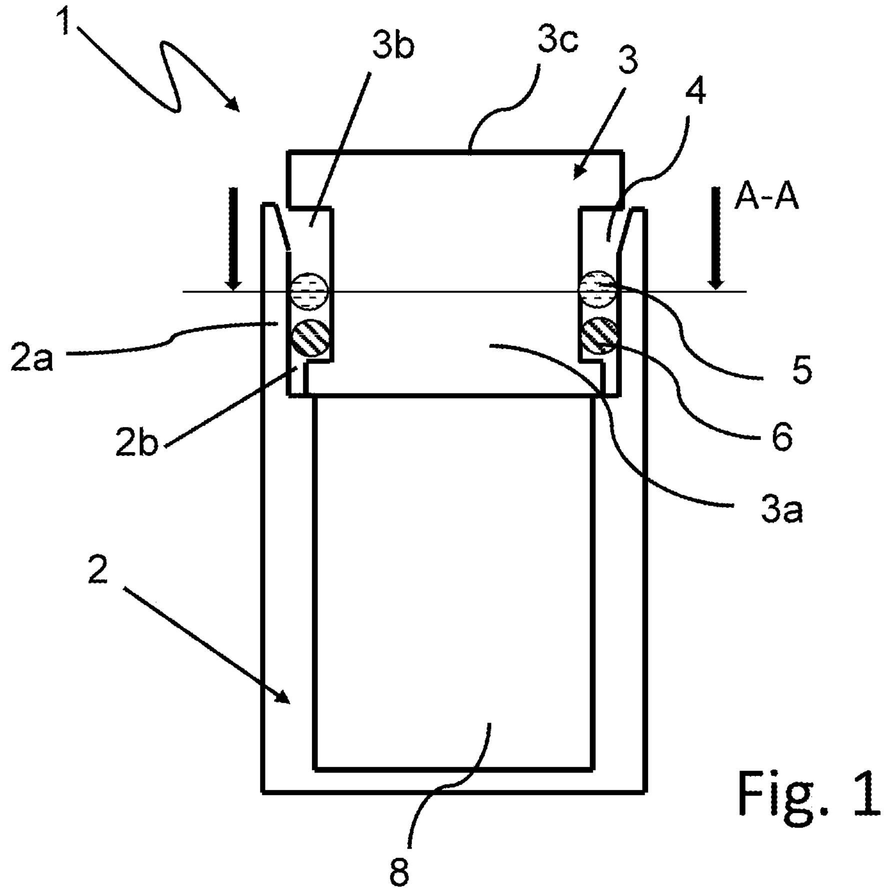
FIG. 1 shows a schematic longitudinal view of a body-wearable medical device.
Figure 2:
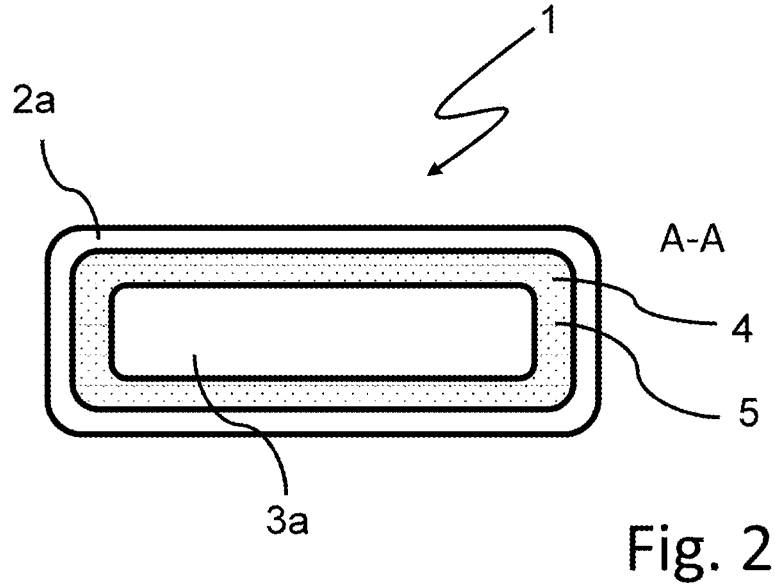
FIG. 2 shows a schematic cross-sectional view of the body-wearable medical device according to FIG. 1.

FIGS. 1 and 2 show a body-wearable medical device 1 according to a first embodiment. FIG. 1 shows a schematic longitudinal view of the body-wearable medical device 1, while FIG. 2 shows a schematic cross-sectional view of the body-wearable medical device 1 along line A-A.

The body-wearable medical device 1 comprises a first housing portion 2 and a second housing portion 3. The first housing portion 2 comprises a female portion **2*a* and the second housing portion 3 comprises a male portion 3*a*. The male portion 3*a* is at least partially inserted into the female portion 2*a*, i.e., the female portion 2*a* forms a receiving portion for accommodating the male portion 3*a* of the second housing portion 3**.

A clearance gap 4 is provided between the male portion **3*a* and the female portion 2*a*, wherein the clearance gap 4 circumscribes the male portion 3*a*. In this embodiment, the clearance gap 4 is at least partially formed by a circumferential recess 3*b* of the male portion 3*a* and a circumferential recess 2*b* of the female portion 2*a*. The circumferential recess 3*b* of the male portion 3*a* and the circumferential recess 2*b* of the female portion 2*a*** are facing each other.

The female portion **2*a* and the male portion 3*a* are fixed to each other by a fixation glue 6 that is evenly distributed within the clearance gap 4 along the circumference of the male portion 3*a*. Next to the fixation glue, a sealing element 5, here a sealing glue, is provided within the clearance gap 4. The sealing element 5 is continuously distributed along the circumference of the male portion 3*a* and in sealing contact with the female portion 2*a* and the male portion 3*a***.

The second housing portion 3, i.e., the housing portion comprising the male portion **3*a*, comprises a free-end 3*c* portion that faces away from the first housing portion 2, i.e., the housing portion comprising the female portion 2***a*. The sealing element 5 is arranged closer to the free-end 3*c* portion than the fixation glue 6. In a direction of insertion of the male portion 3*a* into the female portion 2*b*, the sealing element 5 forms an outer boundary while the fixation glue 6 forms an inner fixation means for holding the male portion 3*a* in fixed position relative to the female portion 2*a*.

The first housing portion 2 and the second housing portion 3 together form a watertight compartment 8.

Figure 3:
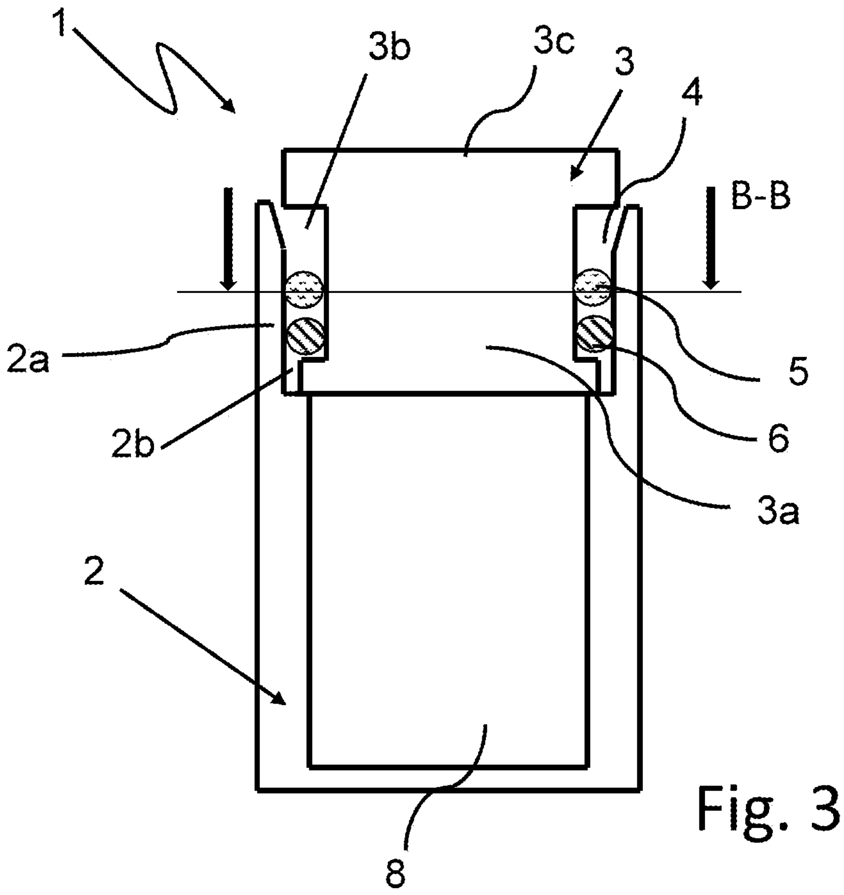
FIG. 3 shows a schematic longitudinal view of a body-wearable medical device according to a further embodiment.
Figure 4:
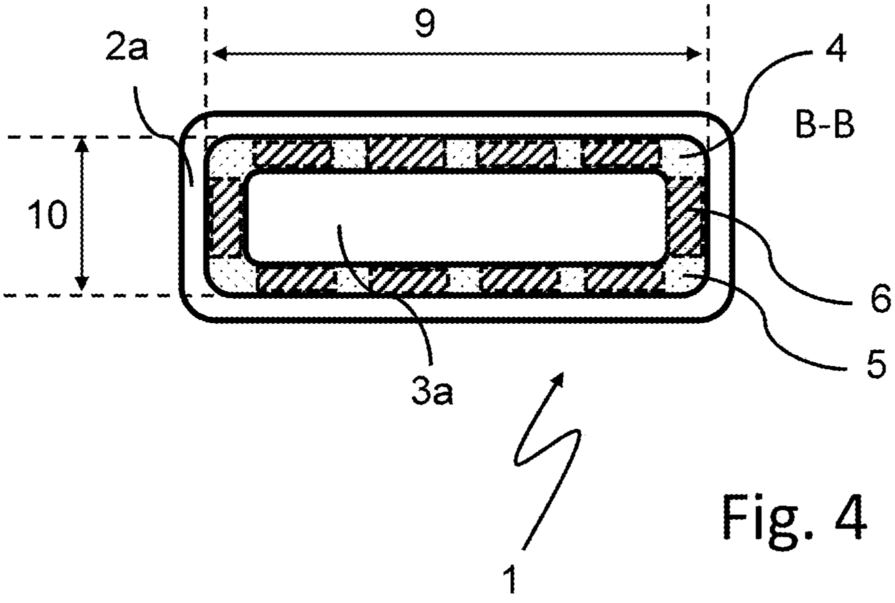
FIG. 4 shows a schematic cross-sectional view of the body-wearable medical device according to FIG. 3.

A second embodiment of a body-wearable medical device 1 is shown by FIGS. 3 and 4. FIG. 3 shows a longitudinal view of the body-wearable medical device 1, while FIG. 4 shows a cross-sectional view of the body-wearable medical device 1 along line B-B.

The body-wearable medical device 1 according FIGS. 3 and 4 differs from the body-wearable medical device 1 according to the embodiment of FIGS. 1 and 2 by having a different configuration of the fixation glue 6.

The fixation glue 6 discontinuously circumscribes the male portion 3*a* within the circumferential gap 4 between the female portion 2*a* and the male portion 3*a*. The fixation glue 6 is formed by multiple fixation glue elements that are evenly distributed along the circumference of the male portion 3*a*. The multiple fixation glue elements forming the fixation glue 6 are indicated in the cross-sectional view of FIG. 4 in broken line for illustrative purposed only as the fixation glue elements are arranged underneath the sealing element 5 and would not be visible in the cross-section along line B-B.

The circumferential clearance gap 4 forms a rectangular-like shape having a first extension 9 in a first direction and a second extension 10 in a second direction. The first extension is at least 1.5 times, here 2 times, larger than the second extension 10 in the second direction. The first direction and the second direction are perpendicular to each other.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

1 body-wearable medical device
2 first housing portion
2*a* female portion
2*b* circumferential recess of female portion
3 second housing portion
3*a* male portion
3*b* circumferential recess of male portion
3*c* free-end portion of male portion
4 circumferential clearance gap
5 circumferential sealing element
6 circumferential fixation glue
7 O-ring
8 compartment
9 first extension in first direction
10 second extension in second direction

What is claimed is:

1. A body-wearable medical device, comprising:

a first housing portion having a female portion and a second housing portion having a male portion, the male portion being at least partially inserted into the female portion, thereby defining a circumferential clearance gap; and a circumferential sealing element arranged in the circumferential clearance gap between the female portion and the male portion;

wherein the female and male portions are fixed to each other by a circumferential fixation glue arranged in the circumferential clearance gap between the female and male portions next to the circumferential sealing element.

2. The body-wearable medical device according to claim 1, wherein the sealing element is a sealing glue having a smaller elastic modulus than the fixation glue.

3. The body-wearable medical device according to claim 1, wherein the sealing element comprises an O-ring arranged in the circumferential clearance gap between the female and male portions and circumscribes the male portion.

4. The body-wearable medical device according to claim 1, wherein the fixation glue discontinuously circumscribes the male portion within the circumferential clearance gap between the female portion and the male portion.

5. The body-wearable medical device according to claim 4, wherein the discontinuously circumscribing fixation glue is evenly distributed along the circumference of the male portion.

6. The body-wearable medical device according to claim 1, wherein the circumferential clearance gap is formed by a circumferential recess of the male portion and/or a circumferential recess of the female portion.

7. The body-wearable medical device according to claim 1, wherein the second housing portion comprises a free-end portion facing away from the first housing portion, wherein the sealing element is located closer to the free-end portion than the fixation glue.

8. The body-wearable medical device according to claim 1, wherein the first and second housing portions form a watertight compartment.

9. The body-wearable medical device according to claim 1, wherein in a cross-sectional view, the circumferential clearance gap forms a rectangular or elliptic shape circumscribing the male portion.

10. The body-wearable medical device according to claim 9, wherein the rectangular or elliptic shape comprises a first extension extending in one direction and a second extension extending in a second direction, wherein the first extension is at least 1.5 times larger than the second extension in the second direction.

* * * * *